United States Patent [19]

Mayfield

[11] 4,386,603

[45] Jun. 7, 1983

[54] DISTRACTION DEVICE FOR SPINAL DISTRACTION SYSTEMS

[76] Inventor: Jack K. Mayfield, 12 Evergreen Rd., St. Paul, Minn. 55110

[21] Appl. No.: 246,299

[22] Filed: Mar. 23, 1981

[51] Int. Cl.³ .............................................. A61F 5/00
[52] U.S. Cl. ...................................... 128/69; 128/75
[58] Field of Search ................... 128/74, 75, 69, 84 B, 128/84 C, 20, 303 B; 254/231-236

[56] References Cited

U.S. PATENT DOCUMENTS

| | | | |
|---|---|---|---|
| 1,373,230 | 3/1921 | Gainor | 254/231 |
| 2,250,417 | 7/1941 | Ettinger | 128/84 B |
| 2,391,537 | 12/1945 | Anderson | 128/84 B |

FOREIGN PATENT DOCUMENTS

| | | | |
|---|---|---|---|
| 2729160 | 1/1978 | Fed. Rep. of Germany | 128/69 |
| 559698 | 6/1977 | U.S.S.R. | 128/69 |

*Primary Examiner*—Richard J. Apley
*Assistant Examiner*—David J. Brown
*Attorney, Agent, or Firm*—Williamson, Bains, Moore & Hansen

[57] ABSTRACT

A distractor device is used to apply force to a pair of distraction hooks each positioned between selected pairs of vertebrae. The hooks are components of a spinal distraction system used in the treatment of spinal deformities or fractures. The distractor device includes a threaded rod having a pair of force applying members shiftably mounted on the rod and each engaging one of the distraction hooks. A threaded nut on the rod engages and causes one of the force applying members to be moved away from the other force applying member to exert a distraction force on the distraction hooks. Each force applying member is pivotally mounted on the rod and is also comprised of a pair of pivotally connected elements whereby the pivoting movement between the force applying members and the rod permits positioning and adjustment of the distractor device in confined spaces.

4 Claims, 6 Drawing Figures

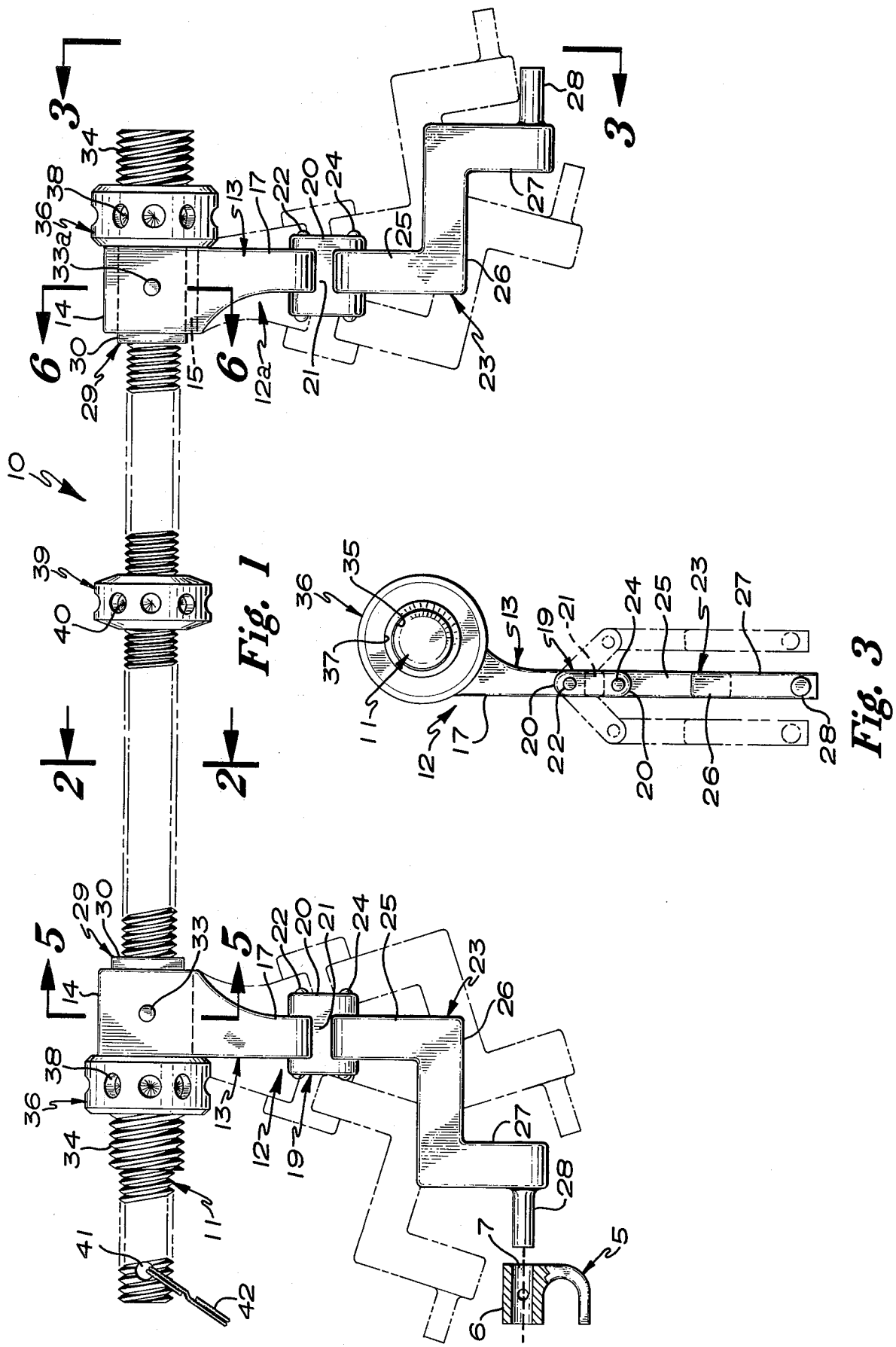

DISTRACTION DEVICE FOR SPINAL DISTRACTION SYSTEMS

SUMMARY OF THE INVENTION

This invention relates to a distractor device which applies a distraction force to distraction hooks used in spinal distraction systems.

It is an object of this invention to provide a distractor device for applying force to a pair of distraction hooks used in spinal distraction systems in which the distractor device is arranged and constructed to permit positioning and manipulation thereof in confined spaces.

A more specific object of this invention is to provide a distractor device for use in spinal distraction systems including a pair of force applying members shiftably mounted on a rod for applying force to a pair of distraction hooks, the force applying members being comprised of pivotally interconnected parts to thereby permit positioning and manipulation of the distractor device in confined spaces.

These and other objects and advantages of this invention will more fully appear from the following description made in connection with the accompanying drawings, wherein like reference characters refer to the same or similar parts throughout the several views.

FIGURES OF THE DRAWINGS

FIG. 1 is a side elevational view of the distractor device with certain parts thereof illustrated in an adjusted position by dotted line configuration;

FIG. 3 is a cross-sectional view taken approximately along line 3—3 of FIG. 1 and looking in the direction of the arrows;

DESCRIPTION OF THE PREFERRED EMBODIMENT OF THE INVENTION

Figure 4:
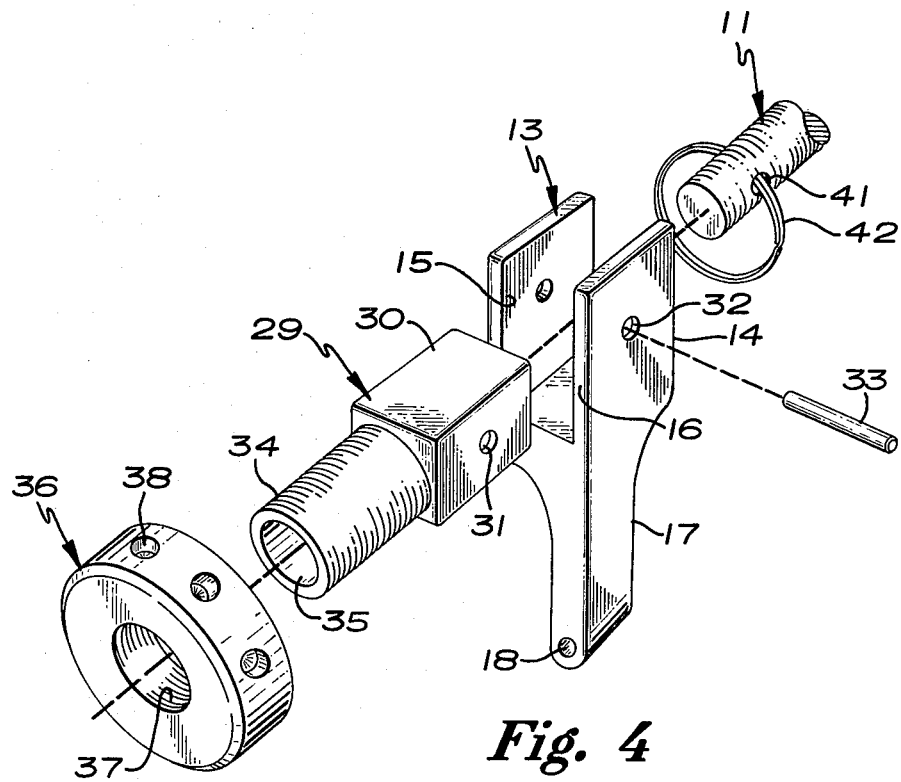
FIG. 4 is an exploded perspective view of a portion of the distractor device illustrating the construction and relationship of certain parts thereof.
Figure 2:
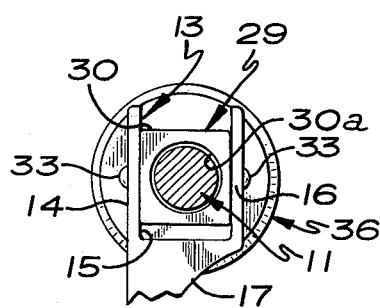
FIG. 2 is a cross-sectional view taken approximately along line 2—2 of FIG. 1 and looking in the direction of the arrows.

Referring now to the drawings, and more specifically to FIG. 1, it will be seen that one embodiment of the distractor device, designated generally by the reference numeral 10, is thereshown. The distractor device 10 is used to apply a rectilinear distraction force to distraction hooks which have been inserted between selected pairs of vertebrae. The distraction hooks are used to transmit a distraction force to the spine from a distraction rod which passes through axial openings in the distraction hooks. This system, known as the Harrington Distraction System (named for the developer, Paul R. Harrington, M.D.), is used in the treatment of patients suffering from scoliosis and spinal fractures. The distraction rod imparts a distraction force to the scoliotic curve to correct the deformity.

The distractor device includes an elongate substantially straight, threaded rod 11 having a movable and a non-movable force applying member 12 and 12a, respectively, mounted thereon. Since the force applying members are substantially identical in construction, a detailed description of only one member is thought to be necessary. Each of force applying members 12 and 12a is comprised of an attachment element 13 including a generally rectangular shaped sleeve 14. The sleeve 14 has a generally U-shaped opening 15 therethrough and presents schematically straight parallel vertical edges 16. Each attachment element 13 also includes a depending arm 17 integral with the sleeve 14 and projecting downwardly therefrom. The lower end of arm 17 is provided with an aperture 18 therethrough, the axis of the aperture 18 being disposed substantially parallel to the general longitudinal axis of the rod 11.

Each force applying member also includes a coupling element 19 which is comprised of a pair of opposed substantially parallel ears 20 interconnected by transverse portion 21. Each of the ears 20 has a pair of openings therein and one opening in each ear is disposed in registering relation with respect to the opening in the other ear and the opening 18 in the depending arm 17. A pivot pin 22 pivotally interconnects the depending arm 17 with the coupling element 19 to permit relative pivotal movement therebetween about an axis which is disposed substantially parallel to the general longitudinal axis of the rod 11.

Each force applying member also includes a hook engaging element 23 which has one end portion thereof pivotally connected by a pivot pin 24 to the coupling element 19. It will be seen that the pivotal axis between the hook engaging element 23 is substantially parallel to the pivotal axis between the coupling element and the attachment element 13. Each hook engaging element which is of angulated construction, includes a substantially straight upper portion 25, a substantially straight transverse portion 26, and a substantially lower portion 27. It will be noted that the upper portion 25 is integral with and disposed in substantially right angular relation with respect to the transverse portion 26. The transverse portion 26 of each hook engaging element is integral with and disposed in substantially right angular relation with the lower portion 27, the latter being disposed in substantially parallel relation with the upper portion 25. The lower portion 27 is provided with a hook engaging pin 28 which is integral with the lower end thereof and which projects in right angular relation therefrom, as best seen in FIG. 1. It will be noted that the hook engaging pin 28 is disposed substantially parallel to the transverse portion 26 and is disposed substantially parallel to the general longitudinal axis of the threaded rod 11.

The pin 28 of each hook engaging element 23 is adapted to project into the axial opening 7 in the hub 6 of the distraction hook 5. It is pointed out that the distraction hook will have been inserted between selected pairs of vertebrae when engaged by the force applying members of the distractor device 10.

Figure 5:
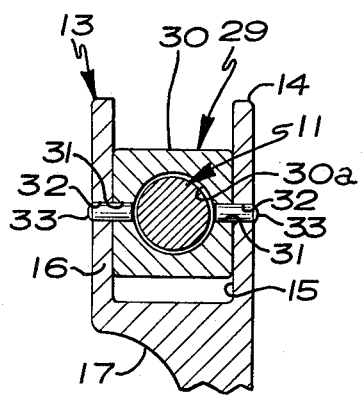
FIG. 5 is a cross-sectional view taken approximately along line 5—5 of FIG. 1 and looking in the direction of the arrows.
Figure 6:
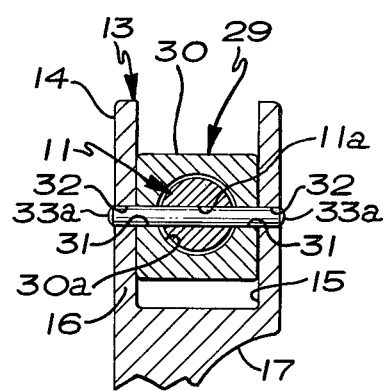
FIG. 6 is a cross-sectional view taken approximately along line 6—6 of FIG. 1 and looking in the direction of the arrows.

The means mounting each of the force applying members 12 and 12a on the threaded rod 11 includes a mounting member 29 which is comprised of a generally rectangular shaped mounting element 30 having a circular bore 30a therethrough as best seen in FIGS. 5 and 6. The rectangular mounting element 30 also has a pair of transverse openings 31 in opposed sides thereof, the openings 31 being disposed in registering relation with respect to each other. The openings 31 in each mounting element 30 are also disposed in registering relation with respect to a pair of openings 32 in the rectangular sleeve 14 of the attachment element 13. In the movable force applying member 12, a pair of pivot pins 33 project into the openings 31 and 32, the pivot pins being disposed in coaxial alignment to pivotally connect the attachment element 13 to the mounting member for pivotal movement about an axis extending substantially normal to the threaded rod 11. In the non-movable force applying member, a single pivot pin 33a projects through the openings 32 in the rectangular sleeve 14, through the openings 31 in the mounting element 30, and through an opening 11a in the rod 11.

Each mounting member 29 also includes an externally threaded sleeve 34 whose opening 35 is disposed in coaxial relation with the bore or opening 30a in the rectangular mounting element 30. The threaded rod 11 projects through the mounting members 29.

Each of the mounting members 29 is provided with a circular stop nut 36, each having a threaded interior 37 which threadedly engage the associated threaded sleeve element 34. It will also be noted that each stop nut 36 is provided with a plurality of circumferentially arranged, diametrically extending openings 38 therein. It will be seen that by shifting each stop nut 36 relative to its associated rectangular sleeve 14, the amount of pivotal movement of the associated force applying member 12 may be adjusted. With this arrangement, the movable force applying member may pivot relative to the rod 11 and moved longitudinally thereof. However, the non-movable force applying member 12a may pivot but may not move longitudinally relative to the rod 11.

Means are also provided for shifting the movable force applying member 12 relative to the threaded rod 11. This means includes a circular nut 39 which threadedly engages the threaded rod 11 for movement relative thereto. The nut 39 is also provided with a plurality of circumferentially arranged, diametrically extending openings 40 therein. It will be seen that when the nut 39 engages the movable force applying member 12, the latter may be urged axially of the threaded rod 11 so that the movable force applying member 12 is shifted away from the non-movable force applying member 12a. Means are also provided for preventing accidental displacement of the movable force applying member 12 relative to the threaded rod 11 and this means includes the stop pin 42 which is secured in an opening 41 in one end of the threaded rod 11.

In use, the pair of distraction hooks 5 will have been inserted between selected pairs of vertebrae. The hook engaging pins 28 will be manipulated until the pins engage in the axial opening 7 in the hooks and the distraction force will then be applied to the hooks by means of the nut 39 engaging the movable force applying member 12.

One of the advantages of the present spreader device over the conventional devices is the ability of the present device to be used in confined spaces. This characteristic of the present device is attributable to the flexing capability of the force applying members relative to the threaded rod 11. In this regard, the ability of each force applying member to pivot about the axes defined by the coupling member allows a wide range of manipulation and positioning of the distraction device in confined spaces attendant with procedures involved in spinal surgery. The ability of the force applying members to pivot about a transverse axis relative to the rod in combination with the flexing capability of the force applying member provides a generally universal type connection between the distractor device and the distraction hooks to be engaged. This advantage is extremely important in spinal surgical procedures.

From the foregoing description, it will be seen that I have provided a novel distractor device, which is not only of simple and inexpensive construction, but one which functions in a more efficient manner than any heretofore known, comparable distractor devices used in spinal distraction systems.

It is anticipated that various changes can be made in the size, shape, and the construction of the distractor device disclosed herein without departing from the spirit and scope of the invention as defined by the following claims.

What is claimed is:

1. A distractor device for exerting force on spaced apart hooks used in a spinal distraction system in which each hook is positioned between a pair of vertebrae, and each hook has an axial opening therethrough, said device comprising:
   an elongate substantially straight threaded rod,
   a movable force applying member and a non-movable force applying member on said rod,
   means mounting said non-movable force applying member on said rod for pivoting movement relative thereto, means mounting said movable force applying member on said rod for pivotal and sliding movement relative thereto, said mounting for said force applying members including a pair of sleeves each positioned around said rod, means pivotally connecting each force applying member with one of said sleeves,
   adjustable stop means for said force applying members cooperating with the latter while limiting pivotal movement of the force applying members, said stop means including a pair of nuts threadedly engaging said rod and each nut engaging one of said sleeves,
   each force applying member including an attachment element and a hook engaging element, means pivotally connecting the attachment and hook engaging element of each force applying member, a hook engaging pin on the hook engaging element of each force applying member for engaging a distraction hook, and means on said rod being movable relative thereto and engagable with said movable force applying member for shifting the same longitudinally of said rod.

2. The distractor device as defined in claim 1 wherein said means for moving said movable force applying member includes a nut threadedly engaging said rod and being engageable with said movable force applying member to shift the latter longitudinally of said rod.

3. A distractor device for exerting force on spaced apart hooks used in a spinal distraction system in which each hook is positioned between a pair of vertebrae, and each hook has an axial opening therethrough, said device comprising:
   an elongate substantially straight threaded rod,
   a movable force applying member and a non-movable force applying member on said rod,
   means mounting said non-movable force applying member on said rod for pivoting movement relative thereto, means mounting said movable force applying member on said rod for pivotal and sliding movement relative thereto,
   adjustable stop means for said force applying members cooperating with the latter while limiting pivotal movement of the force applying members, each force applying member including an attachment element, a coupling element disposed between said attachment element and hook engaging element, means pivotally connecting said coupling element with the attachment element of each force applying member for pivotal movement therebetween about an axis disposed substantially parallel to said rod, means pivotally connecting the coupling element with said hook engaging element for pivotal movement therebetween about an axis disposed substantially parallel to the rod, a hook engaging pin on the hook engaging element of each force applying member for engaging a distraction hook, and means on said rod being movable relative thereto and engagable with said movable force applying member for shifting the same longitudinally of said rod.

4. The distractor device as defined in claim 3 wherein the hook engaging element of each of said force applying members includes an upper portion connected with said coupling element, a transverse portion integral with said coupling element, a transverse portion integral with said upper portion and disposed substantially parallel to said rod, and a lower portion disposed substantially parallel to said upper portion.

* * * * *